United States Patent [19]

Gericke et al.

[11] Patent Number: 6,022,883
[45] Date of Patent: *Feb. 8, 2000

[54] HETEROCYCLYLOXYBENZOYLGUANIDINES

[75] Inventors: Rolf Gericke, Seeheim-Jugenheim; Dieter Dorsch, Ober-Ramstadt; Manfred Baumgarth, Darmstadt; Kläus Otto Minck, Ober-Ramstadt; Norbert Beier, Reinheim, all of Germany

[73] Assignee: Merck Patent Gesellschaft mit Beschrankter Haftung, Darmstadt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/492,619

[22] Filed: Jun. 20, 1995

[30] Foreign Application Priority Data

Jun. 20, 1994 [DE] Germany .................... 44 21 495

[51] Int. Cl.⁷ .................... C07D 213/30; A61K 31/44
[52] U.S. Cl. .................... 514/351; 546/300
[58] Field of Search .................... 546/300; 514/351

[56] References Cited

U.S. PATENT DOCUMENTS

| | | | |
|---|---|---|---|
| 5,292,755 | 3/1994 | Englert et al. | 546/149 |
| 5,364,868 | 11/1994 | Englert et al. | 514/331 |
| 5,373,024 | 12/1994 | Lang et al. | 514/618 |
| 5,461,066 | 10/1995 | Gericke et al. | 514/329 |

FOREIGN PATENT DOCUMENTS

| | | |
|---|---|---|
| 0 416 499 A3 | 9/1990 | European Pat. Off. . |
| 0 556 672 A1 | 2/1993 | European Pat. Off. . |
| 0 589 336 A1 | 9/1993 | European Pat. Off. . |
| 0 600 371 A1 | 11/1993 | European Pat. Off. . |
| 0 602 523 A1 | 12/1993 | European Pat. Off. . |
| 0 612 723 A1 | 2/1994 | European Pat. Off. . |

*Primary Examiner*—John M. Ford
*Attorney, Agent, or Firm*—Miller, White, Zelano, & Branigan, P.C.

[57] ABSTRACT

Heterocyclyloxybenzoylguanidines of the formula I

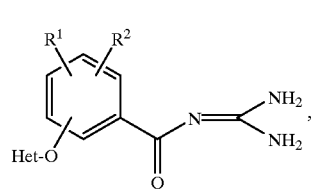

in which $R^1$, $R^2$ and Het have the given meanings, and also the pharmaceutically acceptable salts thereof, exhibit antiarrhythmic properties and act as inhibitors of the cellular $Na^+/H^+$ antiporter.

2 Claims, No Drawings

HETEROCYCLYLOXYBENZOYLGUANIDINES

The invention relates to heterocyclyloxybenzoylguanioylguanidines of the formula I

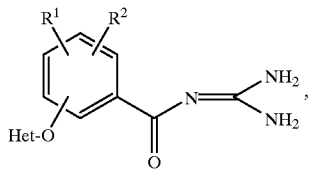

in which $R^1$ and $R^2$ are, in each case independently of each other, H, F, Cl, Br, I, A, CN, $NO_2$, $CF_3$, $C_2F_5$, $CH_2CF_3$, $-SO_n-R^5$, $-SO_2NR^3R^4$, Ph, OPh, Het or $-X-R^3$, $R^3$ is H, A, cycloalkyl having from 5 to 7 C atoms, cycloalkylmethyl having from 6 to 8 C atoms, $CF_3$, $CH_2CF_3$, Ph or $-CH_2-Ph$, $R^4$ is H or A, or else $R^3$ and $R^4$ are together also alkylene having from 4 to 5 C atoms, where one $CH_2$ group can also be replaced by O, S, NH, N—A or N—$CH_2$—Ph, $R^5$ is A or Ph, A is alkyl having 1 to 6 C atoms, X is O, S or $NR^4$, Ph is phenyl which is unsubstituted or is substituted once, twice or three times by A, OA, $NR^3R^4$, F, Cl, Br, I or $CF_3$, Het is a saturated or unsaturated five- or six-membered heterocyclic radical having from 1 to 4 N, O and/or S atoms, which radical can be unsubstituted or substituted once or twice by F, Cl, Br, $CF_3$, A, OH, OA, $NR^3R^4$, $NO_2$, CN and/or carbonyl oxygen

connected via the double bond directly to the heterocyclic ring, and n is 1 or 2, and the pharmaceutically acceptable salts thereof.

The object of the invention was to discover novel compounds having valuable properties, in particular those compounds which can be used for preparing medicaments.

It was found that the compounds of the formula I, and their pharmaceutically acceptable salts, possess valuable pharmacological properties while being well tolerated.

The novel compounds are inhibitors of the cellular $Na^+$/$H^+$ antiporter, i.e., active compounds which inhibit the cellular $Na^+$/$H^+$ exchange mechanism (Düsing et al., Med. Klin. 87, 378–384 (1992)), and thus represent good antiarrhythmic agents which are particularly suitable for treating arrhythmias which arise as a result of lack of oxygen.

The active compound of the acylguanidine group which is most well known is amiloride. However, this substance first and foremost exhibits hypotensive and saluretic effects, which are undesirable when treating disturbances of cardiac rhythm, in particular, whereas the antiarrhythmic properties are only very weakly expressed.

In addition to this, EP 0 416 499, for example, discloses compounds which are structurally similar.

The novel substances of the present application exhibit a good cardioprotective effect and are therefore particularly suitable for the treatment of infarction, for infarction prophylaxis and for treating angina pectoris. In addition, the substances counteract all types of pathological hypoxic and ischemic damage, so that the disorders which are caused primarily or secondarily by such damage can be treated. The active compounds are also well suited for preventive applications.

Because of the protective effects of these substances in pathological hypoxic or ischemic situations, there are further possibilities for using these compounds in association with surgical interventions, for protecting organs which are from time to time less well supplied, in association with organ transplantations, for protecting the organs which are being removed, in association with angioplastic blood vessel or cardiac surgery, in association with ischemias of the nervous system, in association with the therapy of conditions of shock, and for prophylactic prevention of essential hypertension.

In addition, the compounds can also be employed as therapeutic agents in diseases arising from cell proliferation, such as arteriosclerosis, late complications in diabetes, tumor diseases, fibrotic diseases, in particular of the lung, liver and kidneys, and also organ hypertrophies and hyperplasias. In addition to this, these substances are also suitable for being used diagnostically for diagnosing diseases which are associated with an increased activity of the $Na^+$/$H^+$ antiporter, e.g., in erythrocytes, thrombocytes or leucocytes.

The effects of the compounds can be ascertained using methods which are known per se, as described, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Examples of suitable experimental animals are mice, rats, guinea pigs, dogs, cats, monkeys or pigs.

The compounds may, therefore, be used as pharmaceutical active compounds in human and veterinary medicine. In addition, they can be used as intermediates for preparing further pharmaceutical active compounds.

In the given formulae, A is a branched or unbranched alkyl group having 1–6, preferably 1–4, in particular 1, 2 or 3, C atoms, specifically methyl for preference, with ethyl, propyl, isopropyl, butyl or isobutyl also being preferred and sec-butyl, tert-butyl, pentyl, isopentyl (3-methylbutyl), hexyl or isohexyl (4-methylpentyl) furthermore being preferred.

$R^1$ and $R^2$ are preferably independently of each other H, A—$SO_2$, A, $CF_3$, Cl, Br, CN or OA. One of the two radicals is particularly preferably $H_3C$—$SO_2$—, while the other has one of the previously mentioned preferred meanings or else is hydrogen. One of the two radicals $R^1$ and $R^2$ is preferably located in the 3 or 6 position of the benzoyl group. However, an arrangement is particularly preferred in which one radical is located in the ortho position and the other is located in the meta position in relation to the amide group, with, however, the two radicals not, as a rule, being arranged directly adjacent. If one of the radicals is A—$SO_2$—, it is then preferably located in the meta position. A benzoyl group is also particularly preferred which has a methyl-sulfonyl radical in the 3 position and an alkyl group, preferably methyl or ethyl, in the 6 position.

$R^3$ and $R^4$ are preferably H or A.

If $R^3$ and $R^4$ are together alkylene, the alkylene group is then preferably unbranched, specifically $-(CH_2)_k-$ for preference, where k is 4 or 5; however, $-(CH_2)_2-O-(CH_2)_2-$, $-(CH_2)_2-NH-(CH_2)_2-$, $-(CH_2)_2-NA-$ —(CH$_2$)$_2$—, —CH$_2$—O—(CH$_2$)$_2$—, —CH$_2$—NH—(CH$_2$)$_2$—, or —CH$_2$—NA—(CH$_2$)$_2$— or —CO—(CH$_2$)$_3$—, —CO—(CH$_2$)$_4$— or —CH$_2$—CO—(CH$_2$)$_2$ are also preferred.

Ph is preferably phenyl which is unsubstituted or is substituted once by Cl, Br, A, OA, NH$_2$, NHA, NA$_2$ or CF$_3$.

R$^5$ is preferably A, in particular methyl, or else, preferably, also unsubstituted phenyl.

The radical X is preferably O or NH.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, and also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6-, or 7-benzopyrazolyl, 2-, 4-, 5-, 6-, or 7-benzoxazolyl, 3-, 4-, 5-, 6- or 7-benzisoxazolyl, 2-, 4-, 5-, 6-, or 7-benzothiazolyl, 2-, 4-, 5-, 6- or 7-benzisothiazolyl, 4-, 5-, 6-, or 7-benz-2,1,3-oxadiazolyl, 2-, 3-, 4-, 5-, 6-, 7- or 8-quinolinyl, 1-, 3-, 4-, 5-, 6-, 7- or 8-isoquinolinyl, 1-, 2-, 3-, 4-, or 9-carbazolyl, 1-, 2-, 3-, 4-, 5-, 6-, 7- , 8- or 9-acridinyl, 3-, 4-, 5-, 6-, 7- or 8-cinnolinyl or 2-, 4-, 5-, 6-, 7- or 8-quinazolinyl. The heterocyclic radicals can also be partially or completely hydrogenated. Het can therefore also, for example, be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro- 1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl or 1,2,3,4-tetrahydro-1-, -2-, -3-, -4-, -5-, -6-, -7- or -8-isoquinolinyl.

It is true for the whole invention that all radicals such as, for example, Het or Ph which appear many times can be identical or different.

Accordingly, the invention relates, in particular, to those compounds of the formula I in which at least one of the said radicals has one of the above-mentioned, preferred meanings. Some preferred groups of compounds can be expressed by the following formulae Ia to Ih, which conform to the formula I and in which the radicals which are not more precisely described have the meaning given in association with formula I, in which, however, in Ia R$^1$ is H and R$^2$ is —SO$_2$—CH$_3$, —SO$_2$—NH$_2$ or phenoxy in substituted or unsubstituted form;

in Ib R$^1$ is H and R$^2$ is CF$_3$ or CN;

in Ic one of the radicals R$^1$ or R$^2$ is SO$_2$—CH$_3$ and the other radical is A, CF$_3$, Cl, Br, CN or OA;

in Id one of the radicals R$^1$ or R$^2$ is SO$_2$—CH$_3$, and O—Het is 2-, 3- or 4-pyridyloxy which is unsubstituted or is substituted once or twice by A, OH, Cl, Br or NO$_2$;

in Ie one of the radicals R$^1$ or R$^2$ is CF$_3$ or CN, and —O—Het is 3-pyridyloxy;

in If one of the radicals R$^1$ or R$^2$ is SO$_2$—CH$_3$, and —O—Het is 2-pyrazinyloxy, 3- or 4-pyridazinyloxy, 2-pyrimidinyloxy or 4-pyrimidinyloxy;

in Ig the radical O—Het is located in the p-position in relation to the guanidinecarbonyl group, and R$^1$ or R$^2$ is SO$_2$—CH$_3$;

in Ih one of the radicals R$^1$ or R$^2$ is SO$_2$—CH$_3$, while the other is H, A or Cl, and O—Het is 3-pyridyloxy.

The invention also relates to a process for preparing the compounds of the formula I according to claim 1, and the salts thereof, characterized in that a compound of the formula II

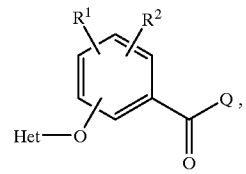

II in which R$^1$, R$^2$ and Het have the previously mentioned meanings, and

Q is Cl, Br, OA, O—CO—A, O—CO—Ph or OH, or another reactive, esterified OH group or leaving group which can readily be substituted nucleophilically, is reacted with guanidine, or in that a benzoylguanidine of the formula III

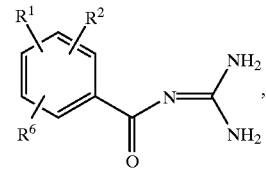

III in which R$^1$ and R$^2$ have the previously mentioned meanings, and R$^6$ is Cl, F, NO$_2$ or another group which can be displaced nucleophilically, is reacted with a heterocyclic compound of the formula IV Het—O—L  IV, in which Het has the given meaning and L is H, (CH$_3$)—Si, an alkali metal cation, NH$^{4+}$, Ag$^+$ or Cu$^+$, or in that a compound which contains one or more reducible group(s) and/or one or more additional C—C and/or C—N bond(s) in place of one or more hydrogen atoms, but which otherwise conforms to the formula I, is treated with a reducing agent, or in that a compound which contains one or more solvolyzable group(s) in place of one or more hydrogen atoms, but which otherwise conforms to the formula I, is treated with a solvolyzing agent, and/or in that a base of the formula I which has been obtained is converted into one of its salts by being treated with an acid.

The compounds of the formula I are otherwise prepared by methods which are known per se, as described in the literature (e.g., in the standard works such as Houben-Weyl, Methoden der organischen Chemie (Methods of Organic Chemistry), Georg-Thieme-Verlag, Stuttgart; Organic Reactions, John Wiley & Sons, Inc., New York; and also in the above-mentioned application EP 0 416 499), and specifically under reaction conditions which are known for the said reactions and which are suitable for these reactions. In this context, use can also be made of variants which are known per se but which have not been mentioned in any detail here.

If desired, the starting compounds may also be formed in situ, such that they are not isolated from the reaction mixture but are instead immediately subjected to further reaction to form the compounds of the formula I.

Preferably, compounds of the formula I are prepared by reacting an activated carboxylic acid derivative of the formula II, where Q is particularly preferably Cl or —O—CH$_3$, with guanidine. Reaction variants are particularly suitable in which the free carboxylic acid II (Q=OH) is converted, in a manner known per se, into the particular activated derivative and this latter is then directly, without intermediate isolation, reacted with guanidine. Examples of methods in which intermediate isolation can be dispensed with are activation with carbonyldiimidazole or dicyclohexylcarbodiimide or the Mukayama variant (Angew. Chem. 91, 788–812 (1979)).

The carboxylic acids of the formula II are prepared by nucleophilic aromatic substitution, proceeding from suitable benzoic acid derivatives, by reaction with corresponding heterocyclic compounds of the formula IV. The reaction is effected in analogy with the reaction of the compounds III and IV. It is described below.

Examples of particularly suitable compounds of the formula IV are 2-, 3- or 4-hydroxypyridines, which can, where appropriate, possess additional substituents, and, in addition, 2-hydroxypyrazines, 2-, 4- or 5-hydroxypyrimidines, or 3- or 4-hydroxy-pyridazines. The trimethylsilyloxy derivatives of the said heterocycles, in particular, are suitable coreactants as compounds of the formula IV.

The reaction of a reactive carboxylic acid derivative of the formula II with guanidine is effected in a manner known per se, preferably in a protic or aprotic, polar or non-polar, inert organic solvent.

Suitable solvents for the reaction of the compounds III and IV are mentioned below. However, particularly preferred solvents are methanol, THF, dimethoxyethane, dioxane or mixtures prepared therefrom, and also water. Temperatures of between 20° and the boiling point of the solvent, for example, are suitable as the reaction temperature. The reaction times are between 5 min. and 12 hrs. It is expedient to include an acid-capturing agent in the reaction. Any type of base which does not interfere with the reaction itself is suitable for this purpose. However, the use of inorganic bases, such as potassium carbonate, or of organic bases, such as triethylamine or pyridine, or else an excess of the guanidine, is particularly suitable.

Compounds of the formula I according to claim 1 can also be prepared by reacting a benzoylguanidine of the formula III with a compound of the formula IV. The starting compounds of the formula III can be prepared, in a simple manner, by reacting appropriately substituted benzoic acids, or reactive acid derivatives, such as, for example, acid halides, esters or anhydrides, which can be derived therefrom, with guanidine under reaction conditions which are known per se for amide preparation and which are generally customary. Particularly suitable reaction variants are again those mentioned beforehand for the reaction of compound II with guanidines.

The compounds of the formula IV are known per se, as are the methods for preparing them. If they are not known, they can be prepared by the methods which are known per se.

The preparation of the compound II, and also the reaction of the compound III with a compound of the formula IV, are effected in a manner known per se, preferably in a protic or aprotic, polar, inert organic solvent.

In the preparation of II, in the reaction of II with guanidine or in the reaction of III with IV, it is likewise expedient to carry out the reaction in the presence of a base or with an excess of the basic component. Preferred examples of suitable bases are alkali metal or alkaline earth metal hydroxides, carbonates or alcoholates, or organic bases such as triethylamine or pyridine, which can also be used in excess and which can then simultaneously serve as solvent.

Suitable inert solvents are, in particular, alcohols, such as methanol, ethanol, isopropanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methyl glycol or ethyl glycol) or ethylene glycol dimethyl ether (diglyme); ketones, such as acetone or butanone; nitriles, such as acetonitrile; nitro compounds, such as nitromethane or nitrobenzene; esters, such as ethyl acetate or hexamethylphosphoric triamide; sulfoxides, such as dimethyl sulfoxide (DMSO); chlorinated hydrocarbons, such as dichloromethane, chloroform, trichloroethylene, 1,2-dichloroethane or carbon tetrachloride; hydrocarbons, such as benzene, toluene or xylene. In addition to this, mixtures of these solvents with each other are also suitable.

A particularly preferred procedure consists of reacting an excess of a heterocyclic compound IV in the form of the trimethylsilyloxy derivative directly, without adding solvents, with a benzoylguanidine of the formula III at temperatures of between 100° and 400°, particularly preferably at from 100° to 200°.

Furthermore, one or more of the radicals $R^1$, $R^2$ and/or Het in a compound of the formula I can be converted into different $R^1$, $R^2$ and/or Het radicals.

For example, it is possible for a H atom to be replaced by a halogen atom, by means of a halogenation, or by a nitro group, by means of a nitration, and/or for a nitro group to be reduced to an amino group, and/or for an amino group or hydroxyl group to be alkylated or acylated, and/or for a benzyl radical to be eliminated hydrogenolytically (e.g., using $H_2$ on a catalyst such as Pd or using ammonium formate in methanol).

A nitration is achieved under customary conditions, for example using a mixture consisting of concentrated $HNO_3$ and concentrated $H_2SO_4$ at temperatures of between 0 and 30°.

This also applies, in an analogous manner, to halogenation, which can be carried out, for example, using elemental chlorine or bromine in one of the customary, inert solvents, at temperatures of between about 0 and 30°.

A primary or secondary amino group and/or an OH group can be converted into the corresponding secondary or tertiary amino group and/or alkoxy group by treating with alkylating agents. Examples of suitable alkylating agents are compounds of the formulae A—Cl, A—Br or A—I, or corresponding sulfuric acid esters or sulfonic acid esters, such as methyl chloride, methyl bromide, methyl iodide, dimethyl sulfate and methyl p-toluenesulfonate. One or two methyl groups can also be introduced, for example, using formaldehyde in the presence of formic acid. The alkylation is expediently undertaken in the presence or absence of one of the said inert solvents, e.g., DMF, at temperatures of between about 0° and about 120°, it also being possible for a catalyst, preferably a base such as potassium tert-butoxide or NaH to be present.

A base of the formula I can be converted into the affiliated acid addition salt using an acid. Acids which are suitable for this reaction are those which give rise to pharmaceutically acceptable salts. Thus, use can be made of inorganic acid, for example sulfuric acid, nitric acid, hydrohalic acids, such as hydrochloric acid or hydrobromic acid, phosphoric acids, such as orthophosphoric acid, or sulfamic acid, and also of organic acids, in particular aliphatic, alicyclic, araliphatic, aromatic or heterocyclic monobasic or polybasic carboxylic acids, sulfonic acids or sulfuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalene monosulfonic and disulfonic acids or laurylsulfuric acid.

The compounds of the formula I and their pharmaceutically acceptable salts may be used to produce pharmaceutical preparations, especially by a non-chemical route, such as by mechanical mixing. When being used for this purpose, they can be brought, together with at least one solid, liquid and/or semiliquid carrier substance or auxiliary substance and, where appropriate, in combination with one or more additional active compound(s), into a suitable dosage form.

The invention furthermore relates to compositions, in particular pharmaceutical preparations, which contain at least one compound of the formula I and/or one of its pharmaceutically acceptable salts.

These preparations can be used as medicaments in human or veterinary medicine. Suitable carrier substances are organic or inorganic substances which are suitable for enteral (e.g., oral), parenteral or topical administration and which do not react with the novel compounds, for example water, vegetable oils, benzyl alcohols, polyethylene glycols, glycerol triacetate, gelatin, carbohydrates, such as lactose or starch, magnesium stearate, talc, lanolin or vaseline. For oral applications, use is made, in particular, of tablets, coated tablets, capsules, syrups, juices or drops, for rectal application of suppositories, for parenteral application of solutions, preferably oily or aqueous solutions, and also of suspensions, emulsions or implants, and for topical application of ointments, creams, pastes, lotions, gels, sprays, foams, aerosols, solutions (e.g., solutions in alcohols, such as ethanol or isopropanol, acetonitrile, DMF, dimethylacetamide or 1,2-propanediol, or their mixtures with each other and/or with water) or powders. The novel compounds can also be lyophilized and the resulting lyophilizates used, for example, to produce preparations for injection.

Liposomal preparations are also especially suitable for topical applications. The given preparations can be sterilized and/or contain auxiliary substances such as glidants, preservatives, stabilizers and/or wetting agents, emulsifiers, salts for influencing the osmotic pressure, buffering substances, coloring substances, flavoring substances and/or aromatizing substances. They can, if desired, also contain one or more additional active compounds, e.g., one or more vitamins.

The compounds of the formula I, and their pharmaceutically acceptable salts, can be administered to humans or animals, in particular mammals such as monkeys, dogs, cats, rats or mice, and be used for the therapeutic treatment of the human or animal body and also for controlling diseases, in particular in association with the therapy and/or prophylaxis of disturbances of the cardiovascular system. They are suitable, therefore, for treating arrhythmias, in particular when the latter are caused by a lack of oxygen, angina pectoris, infarctions, ischemias of the nervous system, such as, for example, stroke or cerebral oedemas, and conditions of shock, and also for preventive treatment.

The substances can also be employed as therapeutic agents in diseases in which cell proliferation plays a role, such as arteriosclerosis, late complications in diabetes, tumor diseases, fibroses and organ hypertrophies and hyperplasias.

In this context, the substances according to the invention are as a rule administered in analogy with known antiarrhythmics, e.g., aprindine, preferably in doses of between about 0.01 and 5 mg, in particular of between 0.02 and 0.5 mg per dosage unit. The daily dose is preferably between about 0.0001 and 0.1, in particular between 0.0003 and 0.01, mg/kg of body weight. Preferred dosages for any particular treatment can be determined by routine testing. However, the special dose for each particular patient depends on a wide variety of factors, for example on the activity of the special compound employed, on the age, on the body weight, on the general state of health, on the sex, on the diet, on the time and route of administration, on the speed of excretion, on the combination of medicines being employed, and on the severity of the particular disease to which the therapy applies. Oral administration is preferred.

In the examples which follow, "customary working-up" denotes:

If required, water is added and extraction takes place using an organic solvent such as ethyl acetate; the organic phase is separated off and dried over sodium sulfate, after which it is filtered and evaporated; the residue is purified by chromatography and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 21 495.2, are hereby incorporated by reference.

EXAMPLES

Example 1

A solution of 540 mg of 3-methylsulfonyl-4-(1,6-dihydro-6-oxo-3-pyridazinyloxy)benzoic acid [obtainable by reacting 3-methylsulfonyl-4-chlorobenzoic acid with 3-trimethylsilyl-oxy-6-oxo-1,6-dihydropyridazine] and 300 mg of carbonyldiimidazole in 15 ml of THF is stirred at room temperature for 2 hours, and 383 mg of guanidine are then added to it. This mixture is then stirred for a further two hours. After the customary working-up, N-diaminomethylene-3-methylsulfonyl-4-(1,6-dihydro-6-oxo-3-pyridazinyloxy)benzamide is obtained, m.p. 268–270°.

The following are obtained in an analogous manner by reacting guanidine with 3-methylsulfonyl-4-(2-pyrimidinyloxy)benzoic acid, N-diaminomethylene-3-methylsulfonyl-4-(2-pyrimidinyloxy)benzamide; with 3-methylsulfonyl-4-(2-pyrazinyloxy)benzoic acid, N-diaminomethylene-3-methylsulfonyl-4-(2-pyrazinyloxy)benzamide, m.p. 253–254°; with 3-methylsulfonyl-4-(4-pyrimidinyloxy)benzoic acid, N-diaminomethylene-3-methylsulfonyl-4-(4-pyrimidinyloxy)benzamide; with 3-methylsulfonyl-4-(5-pyrimidinyloxy)benzoic acid, N-diaminomethylene-3-methylsulfonyl-4-(5-pyrimidinyloxy)benzamide; with 3-methylsulfonyl-4-(3-pyridazinyloxy)benzoic acid, N-diaminomethylene-3-methylsulfonyl-4-(3-pyridazinyloxy)benzamide; with 3-methylsulfonyl-4-(4-pyridazinyloxy)benzoic acid, N-diaminomethylene-3-methylsulfonyl-4-(4-pyridazinyloxy)benzamide; with 3-methylsulfonyl-4-(1,6-dihydro-6-oxo-3-pyridazinyloxy)-6-methylbenzoic acid, N-diaminomethylene-3-methylsulfonyl-4-(1,6-dihydro-6-oxo-3-pyridazinyloxy)-6-methylbenzamide; with 3-methylsulfonyl-4-(1,6-dihydro-6-oxo-3-pyridazinyloxy)-6-ethylbenzoic acid, N-diaminomethylene-3-methylsulfonyl-4-(1,6-dihydro-6-oxo-3-pyridazinyloxy)-6-ethylbenzamide; with 3-methylsulfonyl-4-(1,6-dihydro-6-oxo-3-pyridazinyloxy)-6-chlorobenzoic acid, N-diaminomethylene-3-methylsulfonyl-4-(1,6-dihydro-6-oxo-3-pyridazinyloxy)-6-chlorobenzamide; with 3-methylsulfonyl4-(1,6dihydro-6-oxo-3-pyridazinyloxy)-6-isopropylbenzoic acid, N-diaminomethylene-3-methylsulfonyl-4-(1,6-dihydro-6-oxo-3-pyridazinyloxy)-6-isopropylbenzamide; with 3-methylsulfonyl-4-(1,6-dihydro-6-oxo-3-pyridazinyloxy)-6-trifluoromethylbenzoic acid, N-diaminomethylene-3-methylsulfonyl-4-(1,6-dihydro-6-oxo-3-pyridazinyloxy)-6-trifluoromethylbenzamide.

Example 2

1.1 g of methyl 3-methylsulfonyl-4-(2-pyridyloxy)benzoate [obtainable by reacting 3-methylsulfonyl-4-chlorobenzoic acid with 2-hydroxypyridine and then esterifying the product with methyl iodide/$K_2CO_3$ in dimethylformamide (DMF)] are added to a solution of 928 mg of guanidine in 15 ml of methanol. The mixture is stirred at 50° for 45 minutes, and, after removing the solvent and after the customary working-up, N-diaminomethylene-3-methylsulfonyl-4-(2-pyridyloxy)benzamide is obtained, from which the corresponding hydrochloride, m.p. 247–250°, is obtained following treatment with a dilute. aqueous solution of HCl and freeze drying.

The following are obtained in an analogous manner by reacting guanidine with methyl 3-methylsulfonyl-4-(1-methyl-6-oxo-1,6-dihydro-3-pyridazinyloxy)benzoate, N-diaminomethylene-3-methylsulfonyl-4-(1-methyl-6-oxo-1,6-dihydro-3-pyridazinyloxy)benzamide, hydrochloride, m.p.>270°; m.p. (base) 235–237°; with methyl 3-methylsulfonyl-4-(1-isopropyl-6-oxo-1,6-dihydro-3-pyridazinyloxy)benzoate, N-diaminomethylene-3-methylsulfonyl-4-(1-isopropyl-6-oxo-1,6-dihydro-3-pyridazinyloxy)benzamide, hydrochloride; with methyl 3-methylsulfonyl-4-(3-pyridyloxy)benzoate, N-diaminomethylene-3-methylsulfonyl-4-(3-pyridyloxy)benzamide, hydrochloride, m.p.>250°; m.p. (base) 222–224°; with methyl 3-methylsulfonyl-4-(1-propyl-6-oxo-1,6-dihydro-3-pyridazinyloxy)benzoate, N-diaminomethylene-3-methylsulfonyl-4-(1-propyl-6-oxo-1,6-dihydro-3-pyridazinyloxy)benzamide, hydrochloride; with methyl 3-methylsulfonyl-4-(2-pyridyloxy)-6-methylbenzoate, N-diaminomethylene-3-methylsulfonyl-4-(2-pyridyloxy)-6-methylbenzamide, hydrochloride; with methyl 3-methylsulfonyl-4-(2-pyridyloxy)-6-ethylbenzoate, N-diaminomethylene-3-methylsulfonyl-4-(2-pyridyloxy)-6-ethylbenzamide, hydrochloride; with methyl 3-methylsulfonyl-4-(2-pyridyloxy)-6-chlorobenzoate, N-diaminomethylene-3-methylsulfonyl-4-(2-pyridyloxy)-6-chlorobenzamide, hydrochloride; with methyl 3-methylsulfonyl-4-(3-pyridyloxy)-6-ethylbenzoate, N-diaminomethylene-3-methylsulfonyl-4-(3-pyridyloxy)-6-ethylbenzamide, m.p. 219–223°; with methyl 3-methylsulfonyl-4-(3-pyridyloxy)-6-chlorobenzoate, N-diaminomethylene-3-methylsulfonyl-4-(3-pyridyloxy)-6-chlorobenzamide, m.p. 215–216°; with methyl 3-nitro-4-(3-pyridyloxy)-6-methylbenzoate, N-diaminomethylene-3-nitro-4-(3-pyridyloxy)-6-methylbenzamide,m.p. 197–198°; with methyl 3-methylsulfonyl-4-(1-ethyl-6-oxo- 1,6-dihydro-3-pyridazinyl)benzoate, N-diaminomethylene-3-methylsulfonyl-4-(1-ethyl-6-oxo-1,6-dihydro-3-pyridazinyloxy)benzamide, hydrochloride; with methyl 3-trifluoromethyl-4-(3-pyridyloxy)benzoate, N-diaminomethylene-3-trifluoromethyl-4-(3-pyridyloxy)benzamide, hydrochloride; with methyl 3-cyano-4-(3-pyridyloxy)benzoate, N-diaminomethylene-3-cyano-4-(3-pyridyloxy)benzarmide, hydrochloride; with methyl 3-pentafluoroethyl-4-(3-pyridyloxy)benzoate, N-diaminomethylene-3-pentafluoroethyl-4-(3-pyridyloxy)benzamide, hydrochloride; with methyl 3-(2,2,2-trifluoroethyl)-4-(3-pyridyloxy)benzoate, N-diaminomethylene-3-(2,2,2-trifluoroethyl)-4-(3-pyridyloxy)benzamide, hydrochloride.

Example 3

1.5 g of 4-chloro-N-diaminomethylene-3-methylsulfonyl-6-ethyibenzamide [obtainable by reacting guanidine with 3-methylsulfonyl-4-chloro-6-ethyl-benzoic acid], 10 ml of 3-trimethylsilyloxypyridine and 2.9 g of $K_2CO_3$ are stirred, at 140° for three hours, in small sealed flasks. After cooling, the solid residue is separated off, washed with a little diethyl ether and dissolved in 50 ml of water. After the customary working-up, N-diaminomethylene-3-methylsulfonyl-6-ethyl-4-(3-pyridyloxy)benzamide is obtained, m.p. 219–223°.

Example 4

6.1 g of N-diaminomethylene-3-methylsulfonyl-4-fluorobenzamide [obtainable by reacting methyl 3-methylsulfonyl-4-fluorobenzoate with guanidine] are shaken, at 157° for six hours, in a sealed tube together with 40 ml of 3-trimethylsilyloxypyridine in the presence of 12 g of $K_2CO_3$. After the mixture has been cooled down, the excess silyl compound is decanted off, and the remainder of the mixture is washed with ether. The solid residue is then dissolved in 50 ml of water, and this solution is extracted by shaking with ethyl acetate, and the organic phase is worked up in the normal way. N-Diaminomethylene-3-methylsulfonyl-4-(3-pyridyloxy)benzarmide is obtained, m.p. 222–224°.

Example 5

700 mg of N-diaminomethylene-3-methylsulfonyl-4-(1, 6-dihydro-6-oxo-3-pyridazinyloxy)benzamide (m.p.

268–270°) are suspended in 50 ml of water, and 1.8 ml of 1 N HCl are added to this suspension while it is being stirred. Following filtration and lyophilization, N-diaminomethylene-3-methylsulfonyl-4-(1,6-dihydro-6-oxo-3-pyridazinyloxy)benzamide; hydrochloride are obtained, m.p.>250°.

The following are obtained in an analogous manner from N-diaminomethylene-3-methylsulfonyl-6-ethyl-4-(3-pyridyloxy)benzamide:

N-diaminomethylene-3-methylsulfonyl-6-ethyl-4-(3-pyridyloxy)benzamide, dihydrochloride, m.p.>250°; from N-diaminomethylene-3-methylsulfonyl-4-(3-pyridyloxy) benzamide:

N-diaminomethylene-3-methylsulfonyl-4-(3-pyridyloxy) benzamide, hydrochloride, m.p.>250°.

Example 6

1.0 g of 3-methylsulfonyl-4-(3-pyridyloxy)-6-methylbenzoic acid [obtainable by reacting 3-methylsulfonyl-4-chloro-6-methylbenzoic acid with 3-hydroxypyridine] is dissolved in 15 ml of 1-methylpyrrolidone, and 0.67 g of 1-methyl-2-chloropyridinium chloride is added to this solution, which is stirred for 15 min. 0.9 g of guanidinium chloride and 2.6 ml of N-ethyldiisopropylamine are then added, and the mixture is stirred at room temperature for one hour. Following customary working-up, N-diaminomethylene-3-methylsulfonyl-4-(3-pyridyloxy)-6-methylbenzamide is obtained, m.p. 221–224°.

The following are obtained in an analogous manner from 2-methyl-3-methylsulfonyl-4-(3-pyridyloxy)benzoic acid:

N-diaminomethylene-2-methyl-3-methylsulfonyl-4-(3-pyridyloxy)benzamide, m.p. 214–216°; from 3-methylsulfonyl-4-(3-pyridyloxy)-6-propylbenzoic acid:

N-diaminomethylene-3-methylsulfonyl-4-(3-pyridyloxy)-6-propylbenzamide; from 3-methylsulfonyl-4-(3-pyridyloxy)-6-trifluoromethylbenzoic acid:

N-diaminomethylene-3-methylsulfonyl-4-(3-pyridyloxy)-6-trifluoromethylbenzamide; from 3-methylsulfonyl-4-(3-pyridyloxy)-6-chlorobenzoic acid:

N-diaminomethylene-3-methylsulfonyl-4-(3-pyridyloxy)-6-chlorobenzamide; from 3-methylsulfonyl-4-(3-pyridyloxy)-6-bromobenzoic acid:

N-diaminomethylene-3-methylsulfonyl-4-(3-pyridyloxy)-6-bromobenzamide; from 3-methylsulfonyl-4-(3-pyridyloxy)-6-cyanobenzoic acid:

N-diaminomethylene-3-methylsulfonyl-4-(3-pyridyloxy)-6-cyanobenzamide; from 3-methylsulfonyl-4-(3-pyridyloxy)-6-methoxybenzoic acid:

N-diaminomethylene-3-methylsulfonyl-4-(3-pyridyloxy)-6-methoxybenzamide.

Example 7

In analogy with Example 2, reacting guanidine with methyl 3-methylsulfonyl-4-(6-methyl-3-pyridyloxy) benzoate [obtainable by reacting 3-methylsulfonyl-4-chlorobenzoic acid with 6-methyl-3-trimethylsilyloxypyridine and subsequently esterifying the product with methyl iodide/$K_2CO_3$ in DMF] gives N-diaminomethylene-3-methylsulfonyl-4-(6-methyl-3-pyridyloxy)benzamide, m.p. 197–199°.

The following are obtained in an analogous manner by reacting guanidine with methyl 3-methylsulfonyl-4-(2-nitro-3-pyridyloxy)benzoate, N-diaminomethylene-3-methylsulfonyl-4-(2-nitro-3-pyridyloxy)benzamide; with methyl 3-methylsulfonyl-4-(2-hydroxy-3-pyridyloxy)benzoate, N-diaminomethylene-3-methylsulfonyl-4-(2-hydroxy-3-pyridyloxy)benzamide; with methyl 3-methylsulfonyl-4-(2-hydroxy-5-chloro-3-pyridyloxy)benzoate, N-diaminomethylene-3-methylsulfonyl-4-(2-hydroxy-5-chloro-3-pyridyloxy)benzamide; with methyl 3-methylsulfonyl-4-(5-chloro-3-pyridyloxy)-6-methylbenzoate, N-diaminomethylene-3-methylsulfonyl-4-(5-chloro-3-pyridyloxy)-6-methylbenzamide, m.p. 208–210°; with methyl 3-methylsulfonyl-4-(2-bromo-2-pyridyloxy) benzoate, N-diaminomethylene-3-methylsulfonyl-4-(2-bromo-3-pyridyloxy)benzamide; with methyl 3-methylsulfonyl-4-(4-methyl-3-pyridyloxy)benzoate, N-diaminomethylene-3-methylsulfonyl-4-(4-methyl-3-pyridyloxy)benzamide; with methyl 3-methylsulfonyl-4-(5-chloro-3-pyridyloxy)benzoate, N-diaminomethylene-3-methylsulfonyl-4-(5-chloro-3-pyridyloxy)benzamide, m.p. 233°; with methyl 3-methylsulfonyl-4-(4-hydroxy-3-pyridyloxy)benzoate, N-diaminomethylene-3-methylsulfonyl-4-(4-hydroxy-3-pyridyloxy)benzamide; with methyl 3-methylsulfonyl-4-(2-nitro-4-pyridyloxy)benzoate, N-diaminomethylene-3-methylsulfonyl-4-(2-nitro-4-pyridyloxy)benzamide; with methyl 3-methylsulfonyl-4-(2-hydroxy-4-pyridyloxy)benzoate, N-diaminomethylene-3-methylsulfonyl-4-(2-hydroxy-4-pyridyloxy)benzamide; with methyl 3-methylsulfonyl-4-(2-oxo-1-pyridyloxy)benzoate, N-diaminomethylene-3-methylsulfonyl-4-(2-oxo-1-pyridyloxy)benzamide; with methyl 3-methylsulfonyl-4-(2,5-dioxo-1-pyrrolidinyloxy)benzoate, N-diaminomethylene-3-methylsulfonyl-4-(2,5-dioxo-1-pyrrolidinyloxy)benzamide.

The examples which follow relate to pharmaceutical preparations:

Example A

Injection Vials

A solution of 100 g of an active compound of the formula I and 5 g of disodium hydrogen phosphate in 3 l of double-distilled water is adjusted to pH 6.5 using 2 N hydrochloric acid, sterilized by filtration and used to fill injection vials; the solution in the vials is then lyophilized under sterile conditions and the vials are then sealed in a sterile manner. Each injection vial contains 5 mg of active compound.

Example B

Suppositories

A mixture of 20 g of an active compound of the formula I is melted together with 100 g of soybean lecithin and 1400 g of cocoa butter and the mixture is poured into molds and allowed to cool. Each suppository contains 20 mg of active compound.

Example C

Solution

A solution is prepared consisting of 1 g of an active compound of the formula I, 9.38 g of $NaH_2PO_4.2\ H_2O$, 28.48 g of $Na_2HPO_4.12\ H_2O$ and 0.1 g of benzalkonium chloride in 940 ml of double-distilled water. The solution is adjusted to pH 6.8, made up to 1 l and sterilized by irradiation. This solution can be used in the form of eye drops, for example.

Example D

Ointment 500 mg of an active compound of the formula I is mixed with 99.5 g of vaseline under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed, in a customary manner, into tablets such that each tablet contains 10 mg of active compound.

Example F

Coated tablets

Tablets are compressed in analogy with Example E, which tablets are subsequently coated, in a customary manner, with a coating consisting of sucrose, potato starch, talc, gum tragacanth and coloring matter.

Example G

Capsules

Hard gelatine capsules are filled, in a customary manner, with 2 kg of active compound of the formula I such that each capsule contains 20 mg of the active compound.

Example H

Ampoules

A solution of 1 kg of active compound of the formula I in 60 l of double-distilled water is sterilized by filtration and used to fill ampoules; the solution in the ampoules is lyophilized under sterile conditions and the ampoules are sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Heterocyclyloxybenzoylguanidines of the formula I

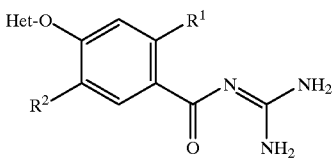

in which $R^1$ is A $R^2$ is $SO_2A$ or $NO_2$,

A is alkyl having 1 to 6 C atoms,

Het is pyridin-3-yl or 5-Cl-pyridin-3-yl, and the physiologically acceptable salts thereof.

2. Pharmaceutical preparation which comprises a compound selected from the group consisting of compounds of the general formula I according to claim 1 and pharmaceutically acceptable salts thereof.

* * * * *